United States Patent
Di Pierro

(10) Patent No.: US 7,201,931 B2
(45) Date of Patent: Apr. 10, 2007

(54) ORAL COMPOSITIONS FOR THE TREATMENT OF SCALP DISORDERS

(75) Inventor: Francesco Di Pierro, Milan (IT)

(73) Assignee: Indena S.p.A., Milan (IT)

( * ) Notice: Subject to any disclaimer, the term of this patent is extended or adjusted under 35 U.S.C. 154(b) by 0 days.

(21) Appl. No.: 10/485,981

(22) PCT Filed: Nov. 14, 2001

(86) PCT No.: PCT/EP01/13188

§ 371 (c)(1),
(2), (4) Date: Aug. 17, 2004

(87) PCT Pub. No.: WO03/013561

PCT Pub. Date: Feb. 20, 2003

(65) Prior Publication Data

US 2005/0008711 A1   Jan. 13, 2005

(30) Foreign Application Priority Data

Aug. 7, 2001   (IT) .......................... MI2001A1732

(51) Int. Cl.
*A01N 65/00* (2006.01)
*A01N 36/00* (2006.01)

(52) U.S. Cl. ..................... 424/766; 424/769; 514/852; 514/864

(58) Field of Classification Search ................ 424/766, 424/769, 70.1, 439, 451, 464, 70.01, 70.2; 514/852, 864, 880
See application file for complete search history.

(56) References Cited

U.S. PATENT DOCUMENTS

| 4,963,527 | A  | * | 10/1990 | Bombardelli et al. |
| 5,895,652 | A  |   | 4/1999  | Giampapa |
| 6,136,860 | A  | * | 10/2000 | Rushton |
| 6,207,694 | B1 | * | 3/2001  | Murad |
| 6,333,057 | B1 | * | 12/2001 | Crandall |

FOREIGN PATENT DOCUMENTS

| FR | 2704394 A1 | * | 11/1994 |
| FR | 2736828 A1 | * | 1/1997 |
| FR | 2816843 A1 | * | 5/2002 |
| JP | 02145509 A | * | 6/1990 |
| WO | WO 97/39632 | * | 10/1997 |
| WO | WO 009139632 A1 | * | 10/1997 |
| WO | 01/30311 |   | 5/2001 |

OTHER PUBLICATIONS

Takahasi, T. et al., Acta Dermat-Venereologica (Nov. 1998). 78(6): 428-432. Proanthocyanidins from grape seeds promote proliferation of mouse hair follicle cells in vitro and convert hair cycle in vivo.*

* cited by examiner

*Primary Examiner*—Michele Flood
(74) *Attorney, Agent, or Firm*—Young & Thompson

(57) ABSTRACT

Pharmaceutical and/or cosmetic compositions for the treatment and the prevention of scalp disorders, containing as active components extracts of *Serenoa repens* and of *Vitis vinifera*.

11 Claims, No Drawings

ORAL COMPOSITIONS FOR THE TREATMENT OF SCALP DISORDERS

The present invention relates to pharmaceutical and/or cosmetic oral compositions for the treatment and the prevention of disorders of the scalp, containing ingredients of vegetable origin.

More particularly, the present invention relates to pharmaceutical and/or cosmetic oral compositions for the treatment and the prevention of disorders of the scalp, containing as active components extracts of *Serenoa repens* and of *Vitis vinifera*.

Dandruff, seborrhea and hair loss or alopecia are among the most common disorders of the scalp.

A number of studies have proved that androgenetic alopecia is a physiological process in genetically predisposed individuals, although its very high frequency, in particular in Caucasians, makes any attempt to establish the heritability mode difficult. Although such heritability is strongly autosomic, the number of the involved genes has not yet been established.

There is evidence of the relationship between androgens and development of androgenetic alopecia: for example, pattern baldness is related with reduced time in hair anagen growth phase, and androgens are known to induce shorter anagen growth phases in scalp hair follicles, which become finer and thinner. Tissue androgens, testosterone and more potent dihydrotestosterone (DHT), can reach the skin through blood circulation or can be locally produced in hair follicles and sebaceous glands by specific enzymes in the steroid cascade. The kinetic constants of a number of enzymes which mediate the formation of DHT, 5-alpha-reductase included, in hair follicles and sebaceous glands of human hair from scalps of man and women affected with androgenetic alopecia have been evaluated; furthermore, androgen receptors specifically binding DHT have been identified in sebocytes and human hair.

Recently, binding studies showed that the dermal papilla of hair follicles of balding subjects contains more androgen receptors than that of normal subjects. As a consequence of this hormone pathway, abnormal sebum secretion may occur, which in turn induces further worsening of baldness as well as overproduction of sebum and dandruff.

Two isoforms of 5-alpha-reductase are known: type 1 and type 2. Prostate contains the type 2 isoenzyme, whereas skin and cutaneous appendages (hair and sebaceous glands)-contain both type 1 and type 2. Finasteride, a type 2 5-alpha-reductase inhibitor originally used for the therapy of prostate hyperplasy, revealed active also in the treatment of androgenetic alopecia; furthermore, a relationship between baldness seriousness and benign prostate hyperplasy seriousness has been observed.

In addition to 5-alpha-reductase, also oxidative stress (pollution, atmospheric agents and the like) and poor intake of oligoelements and sulfated amino acids (such as methionine, cysteine and cystine) through diet adversely affect the hair.

The numerous pharmaceutical or cosmetic formulations for the treatment of dandruff and alopecia at present commercially available have not yet satisfactorily solved these problems.

It has now been found, and this is the object of the present invention, that pharmaceutical and/or cosmetic oral formulations containing a combination of active principles of vegetable origin induce excellent results in the treatment of scalp disorders, in particular alopecia and dandruff, as a result of the combination of the different activities of the various components, which exert, inter alia, antiandrogenic, antiradicalic, antiaging activities.

The compositions of the invention act on the factors which contribute to the development of said scalp disorders, in particular on androgens, oxidative stress, oligoelements and sulfated amino acids present in the diet.

More particularly, the present invention relates to oral pharmaceutical and/or cosmetic compositions containing:

a) extract of *Serenoa repens*, b) standardized extract of *Vitis vinifera*, in the free form and/or as phospholipid complexes.

The components of the compositions of the present invention are all known and used in the pharmaceutical and/or in cosmetic fields. However, it should be noted that the single components, when used separately, exert by far lower activity than that obtained with the compositions of the present invention, in which the various components have been found to exert a synergistic effect of in the prevention and treatment of scalp disorders.

a) The extract of *Serenoa repens* is a vegetable remedy effective in benign prostate hyperplasy due to its antiandrogenic action. This product contains a specific mixture of fatty acids extracted from the plant by means of $CO_2$ in supercritical conditions, as disclosed in EP 250,953, and when tested "in vitro" on prostate isolated cells, it revealed strong affinity to androgen receptors, as demonstrated by displacement with radiolabelled 3H—methyltrienolone.

b) The extract of *Vitis vinifera*, disclosed in GB 1,541,469, includes gallic acid, as well as catechin and epicatechin monomers, dimers, trimers, tetramers, pentamers, hexamers and heptamers in the free form or esterified as gallates. Extensive searches proved its many properties: a) strong, complete antioxidant profile which allow to remove the more reactive radicals, thereby counteracting all the phenomena related to free radicals activity; b) ability to inhibit xanthine-oxidase and to chelate $Cu^{++}$ and $Fe^{++}$, thus preventing the enzymatic release of free radicals into tissues; c) ability to inhibit collagenase, hyaluronidase, elastase and beta-glucuronidase, thus protecting blood vessels and connective tissue against the damages caused by proteolytic enzymes released following UV radiations, oxidative stress and during the development of the inflammatory response.

As mentioned above, the extract of *Vitis vinifera* may also be present in the form of phospholipid complexes as disclosed in U.S. Pat. No. 4,963,527.

The compositions of the present invention may optionally contain, in addition to the above stated components, further ingredients having useful or anyway complementary actions, for example oligoelements, such as zinc, copper, iron, selenium, magnesium; amino acids, such as L-lysine, L-proline, L-hydroxyproline, L-leucine, L-isoleucine, L-methionine, L-cysteine, L-cystine; vitamins, such as the vitamins B complex, vitamin E and vitamin C.

The compositions of the invention will be formulated in oral dosage forms, according to conventional techniques, as described, for example, in *"Remington: The Science and Practice of Pharmacy"*, Lippincott, Williams and Wilkins Eds, December 2000). Said compositions may be in the form of tablets, capsules, oral preparations, powders, granules, lozenges, powders for reconstitution, injectable solutions or suspensions, and liquids for infusions or suppositories.

Tablets and capsules for the oral administration will usually be presented in the form of unitary dosage, and will contain conventional excipients such as binders, diluents, tabletting agents, lubricants, disintegrants, dyes, flavors and wetting agents. Tablets may be coated according to methods well known in the art.

According to an embodiment of the invention, the compositions will be presented in the form of two capsules for the simultaneous administration, one containing the extracts of the invention and the other containing the oligoelements mentioned above.

The oral liquid preparations may, for example, be in the form of aqueous or oily solutions or suspensions, emulsions, syrup or elixir, or dry products for reconstitution with water or other suitable carrier before use. Said liquid preparations may contain conventional excipients such as suspending agents, emulsifiers, non aqueous carriers, preservatives, flavors or dyes.

The compositions of the present invention will be used in such dosage forms as to provide a components daily intake within the following ranges:

a) standardized extract of *Serenoa repens* (40–320 mg/day);

b) standardized extract of *Vitis vinifera* in the free form and/or as phospholipid complexes (50–300 mg/day and 150–900 mg day, respectively).

The oligoelements can be present in such amounts as to provide a daily intake of 0.1 to 100 mg.

The compositions of the invention revealed effective in the treatment of scalp disorders, with beneficial effects on trichogram, dandruff, seborrhea and baldness, and in the prevention of said disorders, ensuring healthy hair.

The results of the pharmacological tests are reported in the following.

Effect on Dandruff, Sebum Production and Hair Loss 60 subjects with dandruff (scaling of the scalp skin) were randomized in four groups. The first received with one capsule prepared according to Example 1 daily for 8 weeks. Evaluations were carried out immediately before starting the treatment, at the end of the treatment (after 8 weeks) and 4 weeks after interrupting the treatment (follow-up). The second group received placebo under the same experimental conditions. The third and the fourth groups received 25 and 80 mg of extracts of *Vitis vinifera* and *Serenoa repens*, respectively.

The results reported in Table 1 evidence that after 8 weeks of treatment the number of desquamated cells (evaluated according to Mac Ginley et al. J. Invest. Dermatol. 53,107, 1969) was reduced from 85 to 18 cells/cm$^2$. The number of desquamated cells was still significantly reduced after 4 weeks of follow-up (21 cells/cm$^2$).

TABLE 1

MAC GINLEY COUNT (cells/cm2)

| Treatment | Start | 8 weeks | 12 weeks |
|---|---|---|---|
| Placebo | 83 ± 3.7 | 85 ± 3.1 | 86 ± 3.6 |
| Capsules of Ex. 1 | 85 ± 2.1 | 18 ± 2.4 | 21 ± 3.1 |
| Extract of *Vitis vinifera* 25 mg | 87 ± 2.9 | 75 ± 3.1 | 80 ± 2.7 |
| Extract of *Serenoa repens* 80 mg | 84 ± 3.1 | 41 ± 4.3 | 63 ± 2.4 |

The results reported in Table 2 prove that the treatment with the capsules of the invention significantly reduces the mean value of scalp sebum from 105 to 92 U.S. (U.S.=arbitrary Sebometric Units). It is particularly remarkable that the value of sebometric units is still significantly reduced (95 U.S.) even 4 weeks after the end of the treatment.

TABLE 2

SEBOMETRY (U.S.)

| Treatment | Start | 8 weeks | 12 weeks |
|---|---|---|---|
| Placebo | 106 ± 7.3 | 105 ± 9.3 | 106 ± 7.9 |
| Capsules of Ex. 1 | 104 ± 8.1 | 92 ± 6.4 | 95 ± 9.3 |
| Extract of *Vitis vinifera* 25 mg | 107 ± 8.3 | 100 ± 6.6 | 103 ± 9.1 |
| Extract of *Serenoa repens* 80 mg | 105 ± 7.9 | 97 ± 7.1 | 99 ± 8.4 |

The effect on hair loss was studied by trichogram evaluation, which consists in taking a sufficient number of hair (about 50) from the higher and antero-nucal frontal areas of each subject (Bosse K., Hautzart, 18, 35, 1967; Bosse K., Hautzart, 18, 218, 1967). The percentage of hair in anagen (growth), catagen (mature), or telogen (rest) phase was evaluated by microscope observation of each single hair shaft under the microscope. Any dystrophic anagen condition, namely the phase in which hair have miniaturized shaft, has also been evaluated in this study. A percentage of hair in telogen phase higher than 10–15% (considered normal) is an index of a clinical pathologic condition of hair loss. The results reported in Table 3 evidence that after 8 week treatment with the capsules of the invention, increase in hair bulbs in anagen phase, decrease in the value of dystrophic anagen hair and, as a consequence, reduction of bulbs in telogen phase were observed. These results were still visible after 4 weeks of follow-up. It should be noted that in the placebo group the clinical situation both at the end of the treatment and after the 4 weeks of follow-up was diametrically opposed.

TABLE 3

EFFECT ON HAIR LOSS

| | PLACEBO | CAPSULES of EX. 1 |
|---|---|---|
| Start | Anagen 82% | Anagen 80% |
| | Catagen 1% | Catagen 1% |
| | Telogen 17% | Telogen 19% |
| | Dystrophic anagen 23% | Dystrophic anagen 20% |
| After 8 weeks of treatment | Anagen 81% | Anagen 82% |
| | Catagen 2% | Catagen 1% |
| | Telogen 17% | Telogen 17% |
| | Dystrophic anagen 22% | Dystrophic anagen 16% |
| After 12 weeks (4 week suspension) | Anagen 80% | Anagen 83% |
| | Catagen 1% | Catagen 1% |
| | Telogen 19% | Telogen 16% |
| | Dystrophic anagen 24% | Dystrophic anagen 17% |

Effect on Seborrheic Dermatitis 40 subjects affected with seborrheic dermatitis of the scalp were randomized in two groups. The first group received a capsule prepared according to Example 1 daily for 8 weeks. Instrumental sebometric evaluation was carried out immediately before starting treatment, at the end of treatment (after 8 weeks), and 4 weeks after suspension of treatment (follow-up). The second group received placebo under the same experimental conditions. The third and fourth groups received 25 and 80 mg of extracts of *Vitis vinifera* and *Serenoa repens*, respectively.

The results reported in Table 4 clearly show that treatment with the capsules of the invention significantly reduced scalp sebum mean value in subjects with seborrheic dermatitis, whose sebum values are above 200 U.S. (U.S.=arbitrary Sebometric Units). This value is still significantly low after 4 weeks of follow-up.

TABLE 4

| Treatment | SEBOMETRY (U.S.) | | |
|---|---|---|---|
| | Start | 8 weeks | 12 weeks |
| Placebo | 233 ± 13 | 210 ± 16 | 240 ± 15 |
| Capsules of Ex. 1 | 241 ± 14 | 135 ± 9 | 150 ± 12 |
| Extract of *Vitis vinifera* 25 mg | 227 ± 9 | 209 ± 14 | 220 ± 13 |
| Extract of *Serenoa repens* 80 mg | 231 ± 13 | 200 ± 16 | 203 ± 16 |

Examples of the compositions according to the invention are reported in the following.

EXAMPLE 1 HARD GELATIN CAPSULES

| Each 326 mg capsule contains: | |
|---|---|
| Extract of *Serenca repens* | 50.0 mg |
| Extract of *Vitis vinifera* extract | 25.0 mg |
| L-cysteine | 30.0 mg |
| L-histidine | 30.0 mg |
| L-methionine | 30.0 mg |
| D-calcium pantotenate | 15.0 mg |
| Zinc citrate (equivalent to 3 mg of zinc) | 10.0 mg |
| Copper citrate (equivalent to 0.8 mg of copper) | 2.3 mg |
| Beta-carotene 10% W.S. (equivalent to 700 U.I. of vitamin A) | 4.3 mg |
| Colloidal silica (Aerosil 200 - DEGUSSA) | 30.0 mg |
| Microcrystalline cellulose (Avicel PH 101 - FMC) | 30.0 mg |
| Maltodextrin (Lycatab DSH - ROQUETTE) | 30.0 mg |
| Pregelatinized starch (Amido STA 1500 - COLORCON) | 21.9 mg |
| Cross-linked sodium carboxymethylcellulose (Ac-Of-Sol - FMC) | 15.0 mg |
| Magnesium stearate | 2.5 mg |

EXAMPLE 2 HARD GELATIN CAPSULES

| Each 326 mg capsule contains: | |
|---|---|
| Extract of *Serenoa repens* | 80.0 mg |
| Extract of *Vitis vinifera* | 25.0 mg |
| Soy polysaccharides (Emcosoy - MENDELL) | 83.0 mg |
| D-calcium pantotenate | 15.0 mg |
| Zinc gluconate (equivalent to 3 mg of zinc) | 23.84 mg |
| Copper gluconate (equivalent to 0.8 mg of copper) | 5.7 mg |
| Colloidal silica (aerosil 200 - DEGUSSA) | 6.2 mg |
| Microcrystalline cellulose (Avicel PH101 - FMC) | 30.0 mg |
| Pregelatinized starch (STA1500 starch - COLORCORN) | 72.0 mg |
| Magnesium stearate | 2.5 mg |

The invention claim is:

1. A method for treating a person having or at risk of developing dandruff or seborrhea, comprising orally administering to said person in need thereof an effective amount of a composition comprising:
    a) extract of *Serenoa repens*; and
    b) extract of *Vitis vinifera* in the free form and/or as phospholipid complexes.

2. The method of claim 1, wherein said composition is in the form of a tablet, capsule, oral preparation, powder, granule, lozenge, solution, suspension, and liquid.

3. The method of claim 1, wherein said composition is administered in combination with additional active ingredients selected from the group consisting of oligoelements, zinc, copper, iron, selenium, magnesium, amino acids, L-lysine, L-proline, L-hydroxyproline, L-leucine, L-isoleucine, L-methionine, L-cysteine, L-cystine, vitamins, vitamin B complex, vitamin E and vitamin C.

4. A method for treating a person having or at risk of developing dandruff or seborrhea, comprising orally administering to said person in need thereof, a composition comprising:
    a) extract of *Serenoa repens* in a daily intake of 40–320 mg/day; and
    b) extract of *Vitis vinifera* in the free form in a daily intake of 50–300 mg/day and/or as phospholipid complexes in a daily intake of 150–900 mg/day.

5. The method of claim 4, wherein said composition is administered in combination with additional active ingredients selected from the group consisting of oligoelements, zinc, copper, iron, selenium, magnesium, amino acids, L-lysine, L-proline, L-hydroxyproline, L-leucine, L isoleucine, L-methionine, L-cysteine, L-cystine, vitamins, vitamin B complex, vitamin E and vitamin C.

6. The method of claim 4, wherein said composition is in the form of a tablet, capsule, oral preparation, powder, granule, lozenge, solution, suspension, and liquid.

7. The method of claim 1, wherein said extract of *Serenoa repens* is administered in the amount of 40–320 mg/day.

8. The method of claim 1, wherein the extract of *Vitis vinifera* is administered in the amount of 50–300 mg/day.

9. The method of claim 1, wherein phospholipid complexes are administered in the amount of 150–900 mg/day.

10. The method according to claim 1, wherein said *Vitis vinifera* is in a phospholipid complex.

11. The method according to claim 4, wherein said *Vitis vinifera* is in a phospholipid complex.

* * * * *